United States Patent [19]

Riera Aixalá

[11] Patent Number: 5,178,830
[45] Date of Patent: Jan. 12, 1993

[54] METHOD OF CLEANING, DISINFECTING AND STERILIZING HEMODIALYSIS APPARATUS

[75] Inventor: José Ma. Riera Aixalá, Granollers, Spain

[73] Assignee: Dibios S.A., Paris, France

[21] Appl. No.: 683,315

[22] Filed: Apr. 10, 1991

Related U.S. Application Data

[63] Continuation-in-part of Ser. No. 421,121, Oct. 13, 1989.

[30] Foreign Application Priority Data

Oct. 13, 1988 [FR] France .................................. 88 13497

[51] Int. Cl.$^5$ .......................... A01L 2/18; A01L 2/20; A01N 59/00; C11D 3/48
[52] U.S. Cl. .................................. 422/37; 422/10; 422/12; 422/13; 422/25; 422/28; 424/661; 424/663; 424/665; 210/501; 134/3; 134/21; 134/22.1; 134/22.13; 134/22.14; 134/22.16; 134/22.17; 134/22.19
[58] Field of Search .................. 422/10, 12, 13, 25, 422/28, 37; 424/661, 663, 665; 210/501; 134/3, 21, 22.1, 22.13, 22.14, 22.16, 22.17, 22.19

[56] References Cited

U.S. PATENT DOCUMENTS

| | | | |
|---|---|---|---|
| 4,084,747 | 4/1978 | Alliger | 422/20 |
| 4,690,772 | 9/1987 | Tell et al. | 424/665 |
| 4,889,654 | 12/1989 | Mason et al. | 422/37 |
| 4,944,920 | 7/1990 | Rubenstein | 422/37 |
| 4,971,760 | 11/1990 | Rubenstein | 422/37 |
| 5,019,402 | 5/1991 | Kross et al. | 422/37 |
| 5,078,967 | 1/1992 | Riera Aixala | 422/37 |

Primary Examiner—Robert J. Warden
Assistant Examiner—Stephanie Blythe
Attorney, Agent, or Firm—Kenyon & Kenyon

[57] ABSTRACT

A method for cleaning, disinfecting and sterilizing hemodialysis apparatus consisting in mixing a basic composition comprising the chlorite ion with an acid composition comprising lactic acid in a mass ratio of the basic composition to the acid composition ranging from 1:6 to 1:3, feeding the mixture thus obtained and admixed with water into the hemodialysis apparatus, the ratio of the mixture to water being of about 1:34 and circulating the final solution in the apparatus wherein the mixture is diluted in water and the basic composition is reacted with the acid composition.

7 Claims, 1 Drawing Sheet

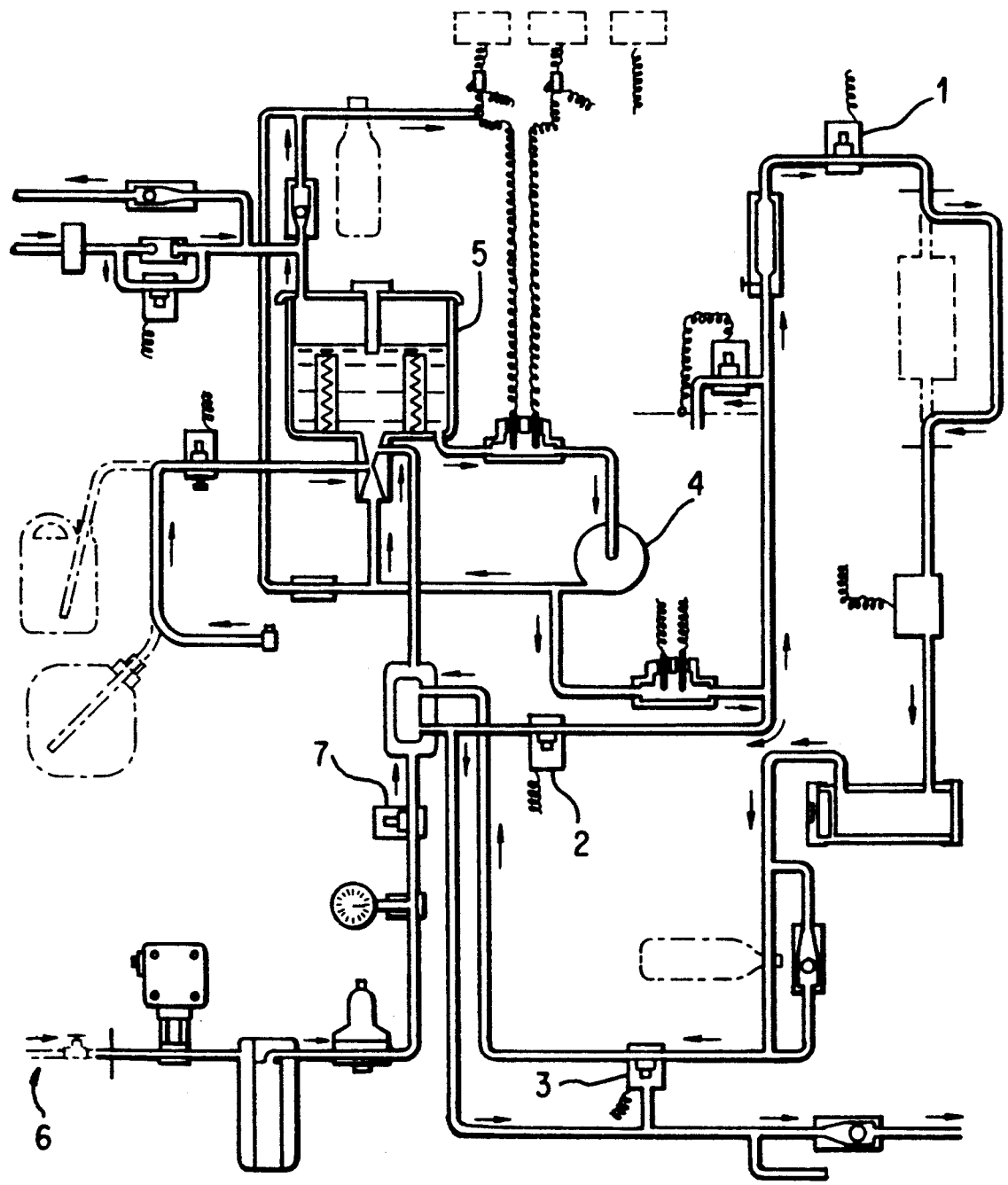

METHOD OF CLEANING, DISINFECTING AND STERILIZING HEMODIALYSIS APPARATUS

This is a Continuation-In-Part of U.S. patent application Ser. No. 07/421,121 filed on Oct. 13, 1989.

BACKGROUND OF THE INVENTION

The present invention relates to the cleaning, the disinfection and the sterilization of hemodialysis apparatus.

Such apparatus are frequently used in the hospitals for the treatment of sick persons suffering from acute or chronic renal insufficiency. These sick persons are indeed subjected to a blood purifying system called hemodialysis which consists in maintaining the ionic equilibrium of the blood, eliminating the products resulting from the metabolism, mainly proteins and maintaining the hydric equilibrium of the organism.

This is carried out by means of the hemodialyser which comprises a semi-permeable membrane which separates two circuits, namely the one where the blood of the patient is flowing and the other one where the dialysis liquid is flowing and which contains a solution based upon an electrolytic composition identical with that of the intercellular liquid. The membrane of this hemodialyser allows the passage of substances of a small and medium molecular size up to molecular masses of 10 to 40,000 daltons.

The operation of the hemodialyser is controlled by an apparatus called hemodialysis control device or still more usually artificial kidney or kidney machine. The latter also performs the function of making the dialysis liquid consisting of a solution of sodium, potassium, calcium and magnesium salts and mixed with a substantial amount of glucose. This liquid is heated up to 37° C. and then flows through the hemodialyser where it receives organic substances originating from the blood through the membrane. These organic substances on the one hand and inorganic substances such as calcium and magnesium salts on the other hand would deposit or precipitate onto the inner surfaces of the circuits of the hemodialysis control device.

Moreover, during the manipulations, small leaks may occur and contaminate or infect the machine. This would result in a substantial hazard of contamination or infection of the patient and of the personnel using this equipment.

It is the reasons why, the hemodialysis apparatus is disinfected after each treatment to remove the bacterial contamination which is developing owing to propicious moisture, temperature, time conditions and in the presence of nutritive substances. Furthermore, owing to the presence of germs in the circuits, it is important to disinfect in view of the substantial risk represented by any infection by the micro-organisms.

Therefore, the cleaning, disinfection and sterilization of a hemodialysis apparatus should meet the following requirements: elimination of mechanical type barriers which would prevent the intimate contact between the disinfecting product and the germs and elimination of the chemical type barriers which would decrease the effect of the disinfecting product.

Accordingly, the problem is to find a cleaning, disinfecting and sterilizing product which has a bactericidal, sporicidal and virucidal activity, which disperses or scatters the organic deposits built up onto the inner surfaces of the circuit, which dissolves the deposits made of inorganic precipitates, which disinfects very effectively the surfaces in a gaseous phase without wetting them, and finally which is compatible with the materials forming the hemodialysis apparatus.

Now conventionally the hemodialysis apparatus are cleaned and disinfected with sodic hypochlorite (salt of the hypochlorous acid) at 5.25% diluted in tap water at a ratio of 1:35. However, sodic hypochlorite is not stable since even within a pH range of 11-12, its active chlore content rapidly decreases. Besides, sodic hypochlorite is generally obtained by electrolysis with means of electrodes one of which is made of mercury, traces of which are found in the sodic hypochlorite solutions used.

Moreover, such a process is carried out under alkaline conditions with a pH between 11 and 12 or above. Therefore, a great number of lipidic or proteinic compounds (most often polypeptides of low molecular weights) such as urea, creatinine, alkaline hydroxides left as a residue of a previous hemodialysis, would precipitate or settle down. Indeed, these compounds as well as the bacteria and the viruses have passed through the semi-permeable membrane of the dialyser from the blood of the sick person to the hemodialysis device. This cleaning operation would be repeated. Consequently, the incrustation of deposits would increase with the number of treatments, and an environment suitable to the microorganisms such as the locations and the porosities of the surfaces in the apparatus, promotes said incrustation of deposits. Cross infections could even be generated in such a case.

After two weeks of continuous use of the dialysis apparatus at a rate of three daily dialysis performances or courses lasting each one 3 or 4 hours with a cleaning-disinfection step between each performance or course (when changing from one patient to another one), the encrusting is such that it is necessary to undertake a more effective cleaning. At this stage, acid solutions are used for removing the encrusted deposits, in other words for descaling the apparatus. Generally, these solutions are based upon oxalic acid or a mixture of oxalic acid and acetic acid. This oxalic acid is used in view of its incrustations-dissolving properties and of its anti-chlorine and anti-rust properties as well as of its absence of corrosive activity on stainless steel, nylon, silicone gum, teflon and glass which are the usual components of these apparatus. When however this de-encrusting phase is completed, any trace of acid should be removed. Oxalic acid being toxic indeed is dangerous for the next patient which undergoes the dialysis.

A washing is then carried out with a solution of bicarbonate which is neutralizing.

However, in spite of the de-encrusting step followed by the neutralizing washing, it is difficult to remove all the traces of virus and bacterium which may remain in the most inaccessible portions of the hemodialysis apparatus such as the gauges or the joints of the various valves.

With such conditions, a last treatment is required: a sterilization with formol, i.e. formaldehyde, every month or every month and one half.

This treatment is carried out in a vapor phase where it is possible to reach invisible places or those places where the liquid does not act because of the air. Generally, the operators are using formol to eliminate a contamination by Pseudomonas aeruginosa.

This cleaning process requires to stop the apparatus for at least 24 hours. Moreover, traces of formol may remain in the apparatus and this is not without danger in view of the mutagen character of formol. Besides, the use of formol is awkward since it is an irritating and toxic agent.

The object of the present invention accordingly is a method of cleaning, disinfecting and sterilizing hemodialysis apparatus in a single step, which would allow to eliminate both the organic deposits and the inorganic precipitates while providing a bactericidal, sporicidal and virucidal activity and a disinfecting activity in a gaseous phase.

The method according to the invention consists in:

mixing a basic composition comprising the chlorite ion with an acid composition comprising lactic acid in a mass ratio of the basic composition to the acid composition ranging from 1:6 to 1:3, feeding the mixture thus obtained and added with water into a hemodialysis apparatus, the volume ratio of the mixture to water being of about 1:34, and circulating the final solution in the apparatus wherein the mixture is diluted in water and the basic composition is reacted with the acid composition.

According to an advantageous feature of the invention, the mass ratio of one basic composition to the acid composition is preferably of about 1:5.

The invention will be better understood and further objects, characterizing features, details and advantages thereof will appear more clearly as the following explanatory description proceeds with reference to the accompanying diagrammatic drawing given by way of non limiting example only illustrating on the single Figure thereof as presently preferred specific embodiment of the invention.

BRIEF DESCRIPTION OF THE DRAWING

This Figure is a diagrammatic showing of the hemodialysis device undergoing a rinsing step.

DETAILED DESCRIPTION OF THE INVENTION

The method of cleaning, disinfecting and sterilizing according to the invention is directed to the use of a solution releasing chlorine dioxide as a disinfecting product within the circuit of the hemodialysis device.

The cleaning, disinfecting medium then becomes acid with a pH ranging from 2.8 to 3.2.

Since the chlorine dioxide at normal temperatures would evaporate quickly and is difficult to be controlled, it is impossible to use it directly.

Even in a state of concentrated gas, it is explosive and harmful or noxious.

Therefore, the method according to the invention using chlorine dioxide is carried out by starting from a basic composition comprising sodic chlorite which will release in the course of a reaction the chlorine dioxide in situ within the hemodialysis apparatus.

More specifically, the method comprises the following steps:

preparation of a basic composition or base solution with from 30% to 50% by weight of sodic chlorite and 70% to 50% by weight of deionized water, preparation of an acid composition or an activating solution with from 70% to 90% by weight of lactic acid and 30% to 10% by weight of deionized water, mixing the base solution with the activating solution in a mass proportion of the base solution to the activating solution ranging from 1:6 to 1:3 and in a mass proportion of preferably about 1:5, while the corresponding volume proportion can range from about 10:1 to about 4:4, diluting the mixture obtained in the foregoing step in running water in a ratio of the mixture to the water of about 1:34, to thereby obtain a dilution of 1/35, and circulating the mixture undergoing dilution in water in the hemodialysis apparatus.

The reaction in two stages which occurs in the apparatus is the following:

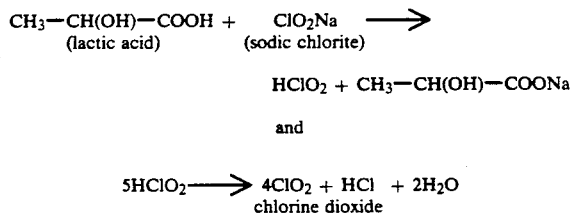

and $$5HClO_2 \longrightarrow 4ClO_2 + HCl + 2H_2O$$
chlorine dioxide

According to this reaction the chlorine dioxide is released within the apparatus.

Now the chlorine dioxide has the peculiarity of being a bactericidal virucidal and sporicidal compound and of having a fixing power or capacity much higher than that of native chlorine. Its biocidal properties are less sensitive to the pH than those of chlorine. This would result in a preservation of its biocidal properties in a much broader range of pH than gaseous chlorine.

To put the invention into practice two products are separately prepared.

The first product, namely the base solution has a composition expressed in percentages of the following type:

| | |
|---|---|
| sodic chlorite at 30%: | 30% to 50% |
| diethylene-glycol: | 1% to 5% |
| trisodic salt of nitrilotriacetic acid at 40%: | 0.2% to 2% |
| deionized water: | complement to 100% |

The density of the sodic chlorite at 30% at 25° C. is 1.20.

The second product, namely the activating solution has a composition expressed in percentages of the following type:

| | |
|---|---|
| lactic acid at 80% of alimentary quality: | 70% to 90% |
| deionized water: | 30% to 10% |

The density of the lactic acid at 80% at 25° C. is 1.18.

Then, the operator would effect the mixing preferably in a mass proportion of the base solution to the acid solution of about 1:5, corresponding to the admixture of 300 milliliters of the base solution with 90 milliliters of the activating solution.

According to a precise and preferred example:

on the hand, a basic solution comprising sodic chlorite (ClO2Na) with a mass/volume ratio of 30%, an initial concentration of 6%, a pure product concentration of 1.80% is prepared in an amount of 5.40 g corresponding to 300 ml; and on the other hand, an activating solution comprising lactic acid with a mass/volume ratio of 80%, an initial concentration of 42%, a pure product concentration of 33.60%, is prepared in an amount of 30.24 g corresponding to 90 ml.

In this case, the mass ratio of the basic solution to the activating solution is 1:5.6.

The mixture thus obtained is fed into the hemodialysis apparatus together with running water.

The dilution and the reaction are occurring during the rinsing cycle of the hemodialysis apparatus according to the single Figure.

Now, the rinsing cycle is preceded by the discharge of the residual fluid from the foregoing cycle.

During the discharge step, the simultaneous opening of the dialysate feed valve 1, of the valve of the flow duct 2 and of the three-way solenoidal valves 3 and the starting of the recirculation pump 4 will allow the flowing of the fluid which remains in the preparation vessel 5 and in all of the ducts of the apparatus.

This phase or step lasts about 2 minutes.

Then, the cleaning, disinfection phase or step itself would begin.

The mixture according to the invention is prepared as described hereinabove in an amount of 390 milliliters.

The dilution of this mixture in running water being equal to 1/35, a total solution of 12.29 liters is fed at 6 into the apparatus.

The introduction of this total solution is carried out continuously or in one single time.

The solenoidal valve 7 would open and when the total solution forming the product used as a disinfectant is flowing throughout the hydraulic circuit, the phase of cleaning-disinfection itself would then be effected, the solenoidal valve 2 in the flow duct would close again while the other ones remain open during the cycle and then would open again at regular intervals. Therefore, the composition forming the disinfecting product is actually flowing throughout the circuit and provides for a cleaning and a perfect disinfection of the flow circuit and of the solenoidal valves.

The dilution therefore takes place inside of the machine and the solution which would result therefrom is circulating there for 10 minutes still at the same concentration.

After 10 minutes the 12.29 liters of the mixture have been passed in the inner circuit of the apparatus because during the same time an equivalent volume has been discharged from the apparatus.

In fact, since the base solution contains a sufficient amount of sodic chlorite, 0.54 gram of sodic chlorite is supplied every minute as well as 3.024 grams of lactic acid, thereby synergizing the solution.

At the end of the cleaning, disinfecting operation after 10 minutes, 5.40 grams of sodic chlorite and 30.24 grams of lactic acid have according flown through the circuit of the hemodialysis apparatus.

It has to be noted that the final concentration of sodic chlorite ($ClO_2Na$), i.e. diluted in 12,290 ml, is 0.044% or 439 ppm of $ClO_2Na$.

And according to the second stage of the reaction mentioned before, the final concentration of chlorine dioxide ($ClO_2$) is 262 ppm.

Following this preferred preparation for the method according to the invention, the disinfecting solution passing through the hemodialysis circuit during ten minutes contains or releases 262 ppm of chlorine dioxide.

Furthermore, throughout this cleaning-disinfection phase, the pH of the solution is kept between 2.8 and 3.2.

With such a value of acid pH, the dissolving of the precipitates which have been left in the apparatus after the hemodialysis treatment is easily carried out. Likewise any trace of life (micro-organisms, virus, spores) has been destroyed and the apparatus then is ready for a new use.

Besides, because of the preferred concentration of chlorine dioxide released in the circuit, the handling of such a method is not awkward for the operator.

The final solution according to the method described hereinabove complies with the following French standards (AFNOR):

antiseptics and disinfectants used in the liquid state, miscible with water and neutralizable, determination of the bactericidal activity (method through dilution-neutralization) (T72-150), antiseptics and disinfectants used in the liquid state, miscible with water and neutralizable, determination of the bactericidal activity in the presence of defined interfering substances (method through dilution-neutralization) (T72-170), disinfectants used in the liquid state, miscible with water, determination of the antibacterial activity for the decontamination of the surfaces (method of the germs-carriers) (T72-190), antiseptics and disinfectants used in the liquid state, miscible with water and neutralizable, determination of the fungicidal activity (method through dilution-neutralization) (T72-200), antiseptics and disinfectants used in the liquid state, miscible with water and killing the bacterial spores, determination of the sporicidal activity in the presence or absence of interfering substances (method through filtration through membranes) (T72-231), methods of decontamination of the surfaces through an aerial process within enclosed spaces, determination of the time of application (T72-281), and antiseptics and disinfectants used in the liquid state, miscible with water, determination of the virucidal activity with respect to bacteriophages (T72-181).

It has moreover been ascertained that the composition such as used in the method according to the invention does not give rise to any corrosion of the elements forming the hemodialysis apparatus.

As a matter of fact, an accelerated test has been carried out, equivalent to 9,000–10,000 hours of operation, i.e. to 3 years of use of the apparatus. The superficial attack, the increase in mass or weight, the physical and operating characteristics of these materials have been determined. No significant corrosion could be noticed on the stainless steel or on the glass, the silicone gum, the nylon nor the teflon.

As to the organic incrustations (proteins with small molecular weights, creatinine, urea, virus) as well as to the inorganic incrustations (carbonates, urates, phosphates, hydroxides, ...), they all have been removed.

A hemodialysis apparatus which exhibited a great accumulation of deposits due to an extended stop in the disinfection system has been subjected to three cleaning performances or courses for 24 hours in accordance with the method according to the invention. At each cleaning cycle, the effectiveness of the product has been ascertained owing to the disappearance of the deposits visible on the surfaces of the crystal tubes of the apparatus.

This method also advantageously replaces the use of formol since it allows to directly cause all the deposits and wastes accumulated by the bacteria, the viruses and the mushrooms to disappear or vanish.

This is illustrated by the following experience. Two devices for controlling the hemodialysis which showed a contamination through Pseudomonas aeruginosa and which had already been disinfected several times with formol solutions at 1% without succeeding in removing this bacterium have been continuously subjected to two disinfecting cycles for 10 hours each one in accordance with the method according to the invention.

Further to the second disinfection cycle, samples have been taken from the devices and present an absence of Pseudomonas aeruginosa.

The method according to the invention is very effective in the gaseous phase, too.

In summary the advantages of the method according to the invention resulting from the cleaning, disinfecting properties of the composition used in the present invention are shown in the following table in comparison with the methods conventionally used.

TABLE

|  | Elimination of inorganic incrustations | Removal of organic deposits | Activity against Pseudomonas Aeruginosa | Activity in a gaseous phase |
| --- | --- | --- | --- | --- |
| Method according to the invention | +++ | +++ | +++ | +++ |
| Method using 50 g of native chlorine per liter | --- | +++ | --+ | --+ |
| Method using formol | --- | --- | -++ | +++ |
| Method using acetic acid | +++ | --+ | -++ | --- |

Under such circumstances in a liquid phase as well as in a gaseous phase the composition used in the method has good bactericidal properties which associated with the cleaning properties are bringing about advantages and an effectiveness well higher than those of the product used in the methods known in the art.

Therefore the periodical (weekly) de-encrusting through acid solutions and the sterilization by means of formol (once a month) are no longer required.

Accordingly, in one single operation, the method according to the invention may replace all the various cleaning, disinfection phases known in the art for the hemodialysis apparatus.

And such a method has a double effect: avoiding inorganic and organic deposits and avoiding the formation of new precipitates.

This very effective method also is very simple and practical in use and provides a substantial gain in time in the departments of nephrology. At last, any danger incurred by the sterilization with formol for the patients and the personnel of the hospitals is removed.

What is claimed is:

1. In a method of cleaning, disinfecting and sterilizing a hemodialysis apparatus having a hemodialysis circuit, said method including steps of feeding a solution into the hemodialysis apparatus and circulating the solution in the apparatus, the improvement which comprises forming said solution by steps comprising
    (a) mixing a basic composition comprising a chlorite ion with an acid composition comprising lactic acid in a mass ratio of the basic composition to the acid composition ranging from 1:6 to 1:3,
    (b) admixing the mixture thus obtained with water, the ratio of the mixture to water being about 1:34.

2. A method according to claim 1, wherein the mass ratio of the basic composition to the acid composition is preferably about 1:5.

3. A method according to claim 1, wherein the basic composition includes from 30% to 50% by weight of sodic chlorite and from 70% to 50% by weight of deionized water.

4. A method according to claim 1, wherein the acid composition contains from 70% to 90% by weight of lactic acid and from 30% to 10% by weight of deionized water.

5. A method according to claim 1, wherein the pH of the final solution flowing in the apparatus is lying between 2.8 and 3.2.

6. A method according to claim 1, wherein the mixture is fed continuously into the hemodialysis apparatus.

7. A method according to claim 1, wherein the the combination of the mixture and water is circulating for 10 minutes in the apparatus.

* * * * *

UNITED STATES PATENT AND TRADEMARK OFFICE
CERTIFICATE OF CORRECTION

PATENT NO. : 5,178,830

DATED : 12 January 1993

INVENTOR(S) : José Ma. Riera Aixala

It is certified that error appears in the above-indentified patent and that said Letters Patent is hereby corrected as shown below:

| Column | Line | |
|---|---|---|
| 4 | 38 | Move "0.2% to 2%" to line 39. |
| 4 | 50 | Move "70% to 90%" to line 51. |
| 4 | 62 | Change "ClO2Na)" to --ClO$_2$Na)--. |

Signed and Sealed this

Twenty-fifth Day of January, 1994

Attest:

BRUCE LEHMAN

Attesting Officer

Commissioner of Patents and Trademarks